United States Patent [19]
Henrick

[11] 4,225,533
[45] Sep. 30, 1980

[54] FLUOROBENZYL ESTERS OF CYCLOPROPANECARBOXYLIC ACIDS

[75] Inventor: Clive A. Henrick, Palo Alto, Calif.

[73] Assignee: Zoecon Corporation, Palo Alto, Calif.

[21] Appl. No.: 44,732

[22] Filed: Jun. 1, 1979

Related U.S. Application Data

[63] Continuation-in-part of Ser. No. 942,509, Sep. 15, 1978.

[51] Int. Cl.³ .................. C07C 69/74; C07C 69/76; C07C 121/66; C07C 121/75

[52] U.S. Cl. .................. 260/465 D; 260/340.5 R; 424/282; 424/304; 424/305; 424/308; 424/309; 560/17; 560/21; 560/61; 560/62; 560/63; 560/124

[58] Field of Search .................. 260/465 D, 340.5 R; 560/17, 61, 124, 21

[56] References Cited

U.S. PATENT DOCUMENTS 4,056,628  11/1977  Winternitz .................. 560/17 X Primary Examiner—Dolph H. Torrence

[57] ABSTRACT

Novel esters of ether and thioether substituted cyclopropanecarboxylic acids, synthesis thereof, and intermediates therefor, such esters being useful as pesticides.

14 Claims, No Drawings

FLUOROBENZYL ESTERS OF CYCLOPROPANECARBOXYLIC ACIDS

This is a continuation-in-part of Ser. No. 942,509, filed Sept. 15, 1978, the entire disclosure of which is incorporated herein by reference.

This invention relates to novel esters of substituted cyclopropane carboxylic acid, synthesis thereof and intermediates therefor, such esters being useful as pesticides.

The novel compounds of the present invention are represented by the following generic formula (A):

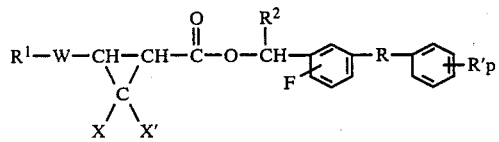

wherein,
W is oxygen or sulfur;
X is lower alkyl or halogen;
X' is hydrogen, lower alkyl or halogen;
R¹ is lower alkyl, lower haloalkyl, lower alkenyl, lower haloalkenyl, or the group

in which,
t is zero, one, two, three or four;
Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro and lower haloalkylthio;
Z is independently selected from the values of Y, cycloalkyl, and lower haloalkoxy; or together with Y forms a methylenedioxy group
R is oxygen, sulfur, methylene or carbonyl;
R' is hydrogen, fluoro, bromo, chloro, trifluoromethyl, methyl, methoxy or methylthio;
p is zero, one or two; and
R² is hydrogen, cyano, methyl or ethynyl.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents known as pyrethrins and synthetic pyrethroids.

In the description hereinafter and the appended claims, each of R through R², W, X, X', Y, Z, p and t is as defined hereinabove, unless otherwise specified.

The compounds of formula (A) can be prepared by the reaction of an acid of formula I or the acid halide thereof with an alcohol of formula IA. For example, the acid I is reacted with thionyl chloride in the presence of a solvent such as hexamethylphosphoric triamide (HMPT), dimethylformamide (DMF), tetrahydrofuran (THF) and the like, and then with the alcohol in the presence of a catalyst such as 4-dimethylaminopyridine.

Alternatively, an acid of formula (I) is reacted with the halide, e.g., bromide, or mesylate corresponding to the alcohol IA in the presence of a base such as potassium carbonate and the like in an organic solvent to prepare the esters of formula A.

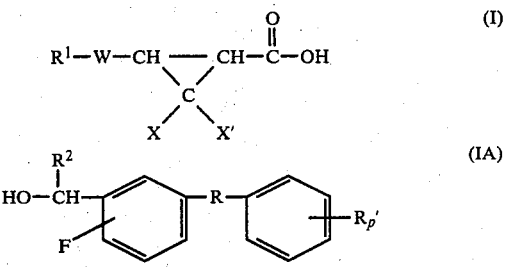

Acids of formula I wherein X is lower alkyl and X' is hydrogen or lower alkyl can be synthesized by the reaction of a vinyl ether or vinyl thioether of formula II with ethyl diazoacetate, either neat or in the presence of a catalyst such as copper or cupric sulfate, to form the ethyl ester III. Cf. *Bull. Soc. Chem.* I, 185 (1956). The ester III is then hydrolyzed to form the acid I.

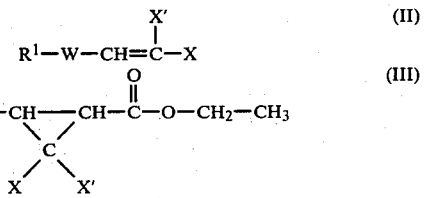

The compounds of formula II wherein W is oxygen, X is lower alkyl and X' is hydrogen or lower alkyl can be synthesized by the reaction of an alcohol R¹—OH with an appropriately alkyl-substituted allylic halide such as 3-chloro-2methyl-1-propene, in the presence of a base such as potassium carbonate in a suitable solvent. The resultant compound of formula IV is then rearranged by reaction with potassium t-butoxide or by reaction with a base such as 1,4-diazobicyclo(2,2,2)octane in the presence of a catalyst such as rhodium trisphenylphosphine chloride to give the vinyl ethers of formula II. Cf. *J. Am. Chem. Soc.* 83, 1701 (1961) and *J. Org. Chem.* 38, 3224 (1973).

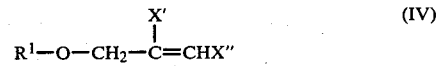

The vinyl thioethers of formula II (W is sulfur, X' is hydrogen or lower alkyl, X" is hydrogen or lower alkyl of one to five) can be synthesized by the reaction of R¹—SH, in the presence of a catalyst, or (CH₃)₃SiCH-(Li)SR¹ with an aldehyde such as 2-methyl-1-propanal. Cf. *J. Org. Chem.* 40, 812 (1975), ibid. 37, 939 (1972), and *Chemistry Letters* (Japan), 479 (1973).

Compounds of formula III wherein each of X and X' is halogen can be made by the reaction of ethyl propiolate with either a thiol R¹—SH or an alcohol R¹—OH to prepare an ester of formula V which is then reacted with phenyl (trihalomethyl) mercury or the like to give the ester III. Cf. *Accounts of Chemical Research* 5, 65 (1972), *Int. J. Sulfur Chem.* 8, 205 (1973), and *Bull. Soc.*

*Chem. France*, 2005 (1974). Alternatively, dihalocarbene can be generated from ethyl trichloroacetate or sodium trichloroacetate.

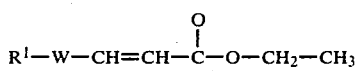
(V)

The alcohols of formula IA can be made as described by Fuchs et al, Offenlegungsschrift Nos. 27 09 264 and 27 39 854, and references cited therein. The alcohols of formula IA or the bromide thereof can be prepared also by reaction of a 3-bromofluorotoluene, e.g., 3-bromo-4 fluorotoluene and phenol or R' substituted phenol with sodium hydride, cuprous chloride, and pyridine using the procedure of A. L. Williams et al., *J. Org. Chem.* 32, 2501 (1967) to form a phenoxy substituted fluorotoluene, e.g., 4-fluoro-3-phenoxytoluene from the reaction of phenol and 3-bromo-4-fluorotoluene. By reaction of the phenoxy-fluorotoluene intermediate with N-bromosuccinimide in the presence of benzoyl peroxide, the bromide is obtained, e.g., 4-fluoro-3-phenoxybenzyl bromide. The bromide can be converted to the corresponding aldehyde, e.g., 4-fluoro-3-phenoxybenzaldehyde, by treatment with sodium bicarbonate in dimethylsulfoxide using the method of Kornblum et al *J. Am. Chem. Soc.* 79, 6562 (1957) or A. P. Johnson et al, *J. Chem. Soc.* 520 (1964). The aldehyde can be converted to the alcohol, e.g., 4-fluoro-3-phenoxybenzyl alcohol, by treatment with lithinum aluminum hydride of sodium borohydride or the like. Compounds of formula IA wherein $R^2$ is cyano can be prepared by reaction of the aldehyde with sodium bisulfite and sodium cyanide by conventional procedures. Compounds of formula IA wherein $R^2$ is ethynyl or methyl can be prepared by Grignard reaction of the aldehyde.

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower alkylthio" refers to an alkylthio group, straight or branched, having a chain length of one to six carbon atoms.

The term "lower alkenyl" refers to an ethylenically unsaturated hydrocarbon group, straight or branched, having a chain length of two to six carbon atoms and one ro two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms.

The term "cycloalkyl" refers to a cycloalkyl group of three to six cyclic carbon atoms.

The term "halogen" refers to bromo, chloro, fluoro or iodo.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula (A) are useful pest control agents, particularly for the control of insects and acarids. In the use of the compounds of formula (A) for combatting insects and acarids for the protection of agricultural crops, for example soybeans, cotton, alfalfa, etc., a compound of formula (A), or mixtures thereof, together with a carrier is applied to the locus in a pesticidally effective amount. The carrier can be liquid or solid and include adjuvants such as wetting agents, dispersing agents and other surface active ingredients. The compounds of formula (A) can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula (A) in the formulation can vary widely, generally within the range of about 0.01 percent to about 90.0 percent, by weight, more usually, 0.01 to 25.0 percent.

The compounds of the present invention can be used in combination with other pesticides such as the carbamates, phosphates and insect growth regulators, e.g., propoxur, carbaryl, naled, dichlorvos, methoprene, kinoprene, hydroprene, cyhexatin, resmethrin, permethrin and fenvalerate.

The following examples are provided to illustrate the practice of the present invention. Temperature is given in degrees Centigrade. RT means room temperature.

EXAMPLE 1

A mixture of 3-(4-chlorophenoxy)-2,2-dimethylcyclopropanecarboxylic acid (0.95 g, 3.95 mmol), thionyl chloride (0.342 ml, 4.74 mmol) and DMF (several drops) in 50 ml benzene is stirred at RT for 2 days. The solvent and excess thionyl chloride are evaporated under reduced pressure. The resulting acid chloride is dissolved in 50 ml benzene, and 0.86 g 4-fluoro-3-phenoxybenzyl alcohol (3.95 mmol) and 0.482 g 4-dimethylaminopyridine (3.95 mmol) are added. The mixture is left at 25° for 18 hours and then heated under reflux for 2 hours. The mixture is then poured into water and extracted with ether. The organic phase is washed with dilute HCl, sat. NaHCO₃, water and brine, dried and concentrated under vacuum. The crude product is purified by preparative TLC developing with 20% ethyl acetate/hexane to yield 4-fluoro-3-phenoxybenzyl 3-(4-chlorophenoxy)-2,2-dimethylcyclopropanecarboxylate.

EXAMPLE 2

The cyanohydrin of 4-fluoro-3-phenoxybenzaldehyde (0.038 mol) is dissolved in 150 ml ether and cooled to 0° in an ice bath. To this is slowly added methanesulfonyl chloride in 20 ml ether. The mixture is stirred for 10 minutes then triethylamine in 20 ml ether is added dropwise. The solution turns white, and a precipitate appears. The reaction mixture is kept at 0° over-night and is then worked up with water and extracted with ether. The ether phase is washed with 30% sodium bisulfite solution (2×), ether and water (2×), and dried over sodium sulfate. The mixture is filtered and the filtrate concentrated to give α-cyano-4 fluoro-3-phenoxybenzyl methanesulfonate.

3-(4-chlorophenoxy)-2,2-dimethylcyclopropanecarboxylic acid (0.82 g, 3.40 mmol) is stirred together with 0.34 g (3.40 mmol) potassium bicarbonate in 10 ml THF/DMF (1:1) for 15 minutes. Then 1.0 g (3.40 mmol) α-cyano-4-fluoro-3-phenoxybenzyl methanesulfonate in 5 ml THF/DMF (1:1) is added and the mixture stirred for approximately 48 hours. The reaction is diluted with ether, washed with water (3×) and sat. NaCl, dried and solvent is removed. The crude product is purified by prep. TLC developing with 10% ethyl acetate/hexane to yield α-cyano-4-fluoro-3-phenoxybenzyl 3-(4-chlorophenoxy)-2,2-dimethylcyclopropanecarboxylate.

EXAMPLE 3

To 10 ml DMF is added 0.88 g 3-(2,2,2-trifluoroethoxy)-2,2-dimethylcyclopropanecarboxylic acid (4.14 mmol) and 1.146 g potassium carbonate (8.29 mmol), after which is added 1.2 g 4-fluoro-3-phenoxybenzyl bromide. This mixture is stirred under nitrogen for 15 hours. The reaction mixture is extracted with ether and the ether phase is washed with water (3×) and brine, and dried over sodium sulfate. The solvent is then removed to yield 4-fluoro-3-phenoxybenzyl 3-(2,2,2-trifluoroethoxy)-2,2-dimethylcyclopropanecarboxylate.

EXAMPLE 4

Each of 3-(4-t-butylphenoxy)-2,2-dimethylcyclopropanecarboxylic acid and 3-(4-methylphenoxy)-2,2-dimethylcyclopropanecarboxylic acid is reacted with thionyl chloride and then with 4-fluoro-3-phenoxybenzyl alcohol to yield, respectively, 4-fluoro-3-phenoxybenzyl 3-(4-t-butylphenoxy)-2,2-dimethylcyclopropanecarboxylate and 4-fluoro-3-phenoxybenzyl 3-(4-methylphenoxy)-2,2-dimethylcyclopropanecarboxylate.

EXAMPLE 5

Each of the carboxylic acids listed under column I is reacted with 4-fluoro-3-phenoxybenzyl bromide using the procedure of Example 3 to yield the respective ester under column II

I 3-(4-chloro-2-fluorophenoxy)-2,2-dimethylcyclopropanecarboxylic acid
3-(2-trifluoromethylphenoxy)-2,2-dimethylcyclopropanecarboxylic acid
3-(4-trifluoromethylphenoxy)-2,2-dimethylcyclopropanecarboxylic acid
3-(2-fluorophenoxy)-2,2-dimethylcyclopropanecarboxylic acid
3-(2,4-difluorophenoxy)-2,2-dimethylcyclopropanecarboxylic acid
3-(2-chlorophenoxy)-2,2-dimethylcyclopropanecarboxylic acid
3-(2-methylphenoxy)-2,2-dimethylcyclopropanecarboxylic acid
3-(2-chloro-4-methylphenoxy)-2,2-dimethylcyclopropanecarboxylic acid
3-(4-chloro-2-nitrophenoxy)-2,2-dimethylcyclopropanecarboxylic acid
3-(2-fluoro-4-trifluoromethylphenoxy)-2,2-dimethylcyclopropanecarboxylic acid
3-(4-bromo-2-chlorophenoxy)-2,2-dimethylcyclopropanecarboxylic acid

II 4-fluoro-3-phenoxybenzyl 3-(4-chloro-2-fluorophenoxy)-2,2-dimethyl-cyclopropanecarboxylate
4-fluoro-3-phenoxybenzyl 3-(2-trifluoromethylphenoxy)-2,2-dimethyl-cyclopropanecarboxylate
4-fluoro-3-phenoxybenzyl 3-(4-trifluoromethylphenoxy)-2,2-dimethyl-cyclopropanecarboxylate
4-fluoro-3-phenoxybenzyl 3-(2-fluorophenoxy)-2,2-dimethyl-cyclopropanecarboxylate
4-fluoro-3-phenoxybenzyl 3-(2,4-difluorophenoxy)-2,2-dimethyl-cyclopropanecarboxylate
4-fluoro-3-phenoxybenzyl 3-(2-chlorophenoxy)-2,2-dimethyl-cyclopropanecarboxylate
4-fluoro-3-phenoxybenzyl 3-(2-methylphenoxy)-2,2-dimethyl-cyclopropanecarboxylate
4-fluoro-3-phenoxybenzyl 3-(2-chloro-4-methylphenoxy)-2,2-dimethyl-cyclopropanecarboxylate
4-fluoro-3-phenoxybenzyl 3-(4-chloro-2-mitrophenoxy)-2,2-dimethyl-cyclopropanecarboxylate
4-fluoro-3-phenoxybenzyl 3-(2-fluoro-4-trifluoromethylphenoxy)-2,2-dimethyl-cyclopropanecarboxylate
4-fluoro-3-phenoxybenzyl 3-(4-bromo-2-chlorophenoxy)-2,2-dimethyl-cyclopropanecarboxylate

EXAMPLE 6

Following the procedure of Example 2, 3-(4-methylphenoxy)-2,2-dimethylcyclopropanecarboxylic acid is reacted with α-cyano-4-fluoro-3-phenoxybenzyl methanesulfonate to yield α-cyano-4-fluoro-3-phenoxybenzyl 3-(4-methylphenoxy)-2,2-dimethylcyclopropanecarboxylate.

EXAMPLE 7

Following the procedure of Example 2, each of the acids listed under column I is reacted with α-cyano-4-fluoro-3-phenoxybenzyl methanesulfonate to yield the respective esters in column III.

III

α-cyano-4-fluoro-3-phenoxybenzyl 3-(4-chloro-2-fluorophenoxy)-2,2-dimethylcyclopropanecarboxylate
α-cyano-4-fluoro-3-phenoxybenzyl 3-(2-trifluoromethylphenoxy)-2,2-dimethylcyclopropanecarboxylate
α-cyano-4-fluoro-3-phenoxybenzyl 3-(4-trifluoromethylphenoxy)-2,2-dimethylcyclopropanecarboxylate
α-cyano-4-fluoro-3-phenoxybenzyl 3-(2-fluorophenoxy)-2,2-dimethylcyclopropanecarboxylate
α-cyano-4-fluoro-3-phenoxybenzyl 3-(2,4-difluorophenoxy)-2,2-dimethylcyclopropanecarboxylate
α-cyano-4-fluoro-3-phenoxybenzyl 3-(2-chlorophenoxy)-2,2-dimethylcyclopropanecarboxylate
α-cyano-4-fluoro-3-phenoxybenzyl 3-(2-methylphenoxy)-2,2-dimethylcyclopropanecarboxylate
α-cyano-4-fluoro-3-phenoxybenzyl 3-(2-chloro-4-methylphenoxy)-2,2-dimethylcyclopropanecarboxylate
α-cyano-4-fluoro-3-phenoxybenzyl 3-(4-chloro-2-nitrophenoxy)-2,2-dimethylcyclopropanecarboxylate
α-cyano-4-fluoro-3-phenoxybenzyl 3-(2-fluoro-4-trifluoromethylphenoxy)-2,2-dimethylcyclopropanecarboxylate
α-cyano-4-fluoro-3-phenoxybenzyl 3-(4-bromo-2-2chlorophenoxy)-2,2-dimethylcyclopropanecarboxylate

EXAMPLE 8

To a mixture of 3-(4-chlorophenoxy)-2,2-dimethylcyclopropanecarboxylic acid (2.77 mmol), potassium carbonate (3.25 mmol) and hexamethylphosphoric triamide (HMPT) (3 ml), with stirring and under nitrogen, at RT, is added 2-fluoro-5-phenoxybenzyl bromide (2.77 mmol) in THF. The reaction is stirred at RT for about 48 hours and then worked up by partition between water/ether. The organic phase is washed with water and brine, dried over potassium carbonate, filtered and the solvent is removed from the filtrate. The residue is plated on prep. TLC plates developing with 10% ether/hexane to yield 2-fluoro-5-phenoxybenzyl 3-(4-chlorophenoxy)-2,2-dimethylcyclopropanecarboxylate.

EXAMPLE 9

Following the method of Example 3, each of the acids of column IV

IV 3-n-propoxy-2,2-dimethylcyclopropanecarboxylic acid
3-but-2-enoxy-2,2-dimethylcyclopropanecarboxylic acid
3-(3-fluoropropenoxy)-2,2-dimethylcyclopropanecarboxylic acid
3-(t-butoxy)-2,2-dimethylcyclopropanecarboxylic acid
3-(4-chloro-3-fluorobut-2-enoxy)-2,2-dimethylcyclopropanecarboxylic acid is reacted with 4-fluoro-3-phenoxybenzyl bromide, as in Example 3, to yield the 4-fluoro-3-phenoxybenzyl ester (column V).

V 4-fluoro-3-phenoxybenzyl 3-n-propoxy-2,2-dimethylcyclopropanecarboxylate
4-fluoro-3-phenoxybenzyl 3-but-2-enoxy-2,2-dimethylocyclopropanecarboxylate
4-fluoro-3-phenoxybenzyl 3-(3-fluoropropenoxy)-2,2-dimethlcyclopropanecarboxylate
4-fluoro-3-phenoxybenzyl 3-(t-butoxy)-2,2-dimethylcyclopropanecarboxylate
4-fluoro-3-phenoxybenzyl 3-(4-chloro-3-fluorobut-2-enoxy)-2,2-dimethylcyclopropanecarboxylate

EXAMPLE 10

Following the procedure of Example 3, 3-(4-fluorophenoxy)-2,2-dimethylcyclopropanecarboxylic acid is reacted with each of 3-fluoro-5-phenoxybenzyl bromide, 4-fluoro-3-(4-fluorophenoxy) benzyl bromide and 2-fluoro-5-phenoxybenzyl bromide to yield, respectively, 3-fluoro-5-phenoxybenzyl 3-(4-fluorophenoxy)-2,2-dimethylcyclopropanecarboxylate, 4-fluoro-3-(4-fluorophenoxy) benzyl 3-(4-fluorophenoxy)-2,2-dimethylcyclopropanecarboxylate, and 2-fluoro-5-phenoxybenzyl 3-(4-fluorophenoxy)-2,2-dimethylcyclopropanecarboxylate.

In the same manner, 4-fluoro-3-phenoxybenzyl 3-(n-butoxy)-2,2-dimethylcyclopropanecarboxylate is produced from 3-(n-butoxy)-2,2-dimethylcyclopropanecarboxylic acid and 4-fluoro-3-phenoxybenzyl bromide.

Using the method of Example 3, 3-phenylthio-2,2-dimethylcyclopropanecarboxylic acid is reacted with 4-fluoro-3-phenoxybenzyl bromide to yield 4-fluoro-3-phenoxybenzyl 3-phenylthio-2,2-dimethylcyclopropanecarboxylate.

The carboxylic acid 3-phenoxy-2,2-dichlorocyclopropanecarboxylic acid is reacted with each of 4-fluoro-3-phenoxybenzyl bromide and α-cyano-4-fluoro-3-phenoxybenzyl methanesulfonate to yield, respectively, 4-fluoro-phenoxybenzyl 3-phenoxy-2,2-dichlorocyclopropanecarboxylate and a-cyano-4-fluoro-3-phenoxybenzyl 3-phenoxy-2,2-dichlorocyclopropanecarboxylate.

EXAMPLE 11

Each of the acids, 3-phenylthio-2,2-dichlorocyclopropanecarboxylic acid, 3-(4-fluorophenylthio)-2,2-difluorocyclopropane carboxylic acid, and 3-(n-pentylthio)-2,2-dimethylcyclopropanecarboxylic acid is reacted with 4-fluoro-3-phenoxybenzyl bromide using the procedure of Example 3 to yield 4-fluoro-3-phenoxybenzyl 3-phenylthio-2,2-dichlorocyclopropanecarboxylate, 4-fluoro-3-phenoxybenzyl 3-(4-fluorophenylthio)-2,2-difluorocyclopropanecarboxylate and 4-fluoro-3-phenoxybenzyl 3-(n-pentylthio)-2,2-dimethylcyclopropanecarboxylate, respectively.

EXAMPLE 12

Following the procedure of Example 1, each of 4-fluoro-3-phenoxybenzyl alcohol, 2-fluoro-5-phenoxybenzyl alcohol, 3-(4-fluorophenoxy)-4-fluorobenzyl alcohol and 4-fluoro-3-(4-methylphenoxy) benzyl alcohol is reacted with 3-(n-pentyloxy)-2,2-dimethylcyclopropanecarboxylic acid to yield:
4-fluoro-3-phenoxybenzyl 3-(n-pentyloxy)-2,2-dimethylcyclopropanecarboxylate,
2-fluoro-5-phenoxybenzyl 3-(n-pentyloxy)-2,2-dimethylcyclopropanecarboxylate,
3-(4-fluorophenoxy)-4-fluorobenzyl 3-(n-pentyloxy)-2,2-dimethylcyclopropanecarboxylate, and
4-fluoro-3-(4-methylphenoxy) benzyl 3-(n-pentyloxy)-2,2-dimethylcyclopropanecarboxylate.

EXAMPLE 13

During the procedure of Example 2, each of the acids
3-(n-pentyloxy)-2,2-dimethylcyclopanecarboxylic acid,
3-(n-propoxy)-2,2-dimethylcyclopanecarboxylic acid,
3-(n-butoxy)-2,2-dimethylcyclopanecarboxylic acid, and
3-(n-hexyloxy)-2,2-dimethylcyclopanecalboxylic acid is reacted
with α-cyano-4-fluoro-3-phenoxybenzyl bromide to yield:
α-cyano-4-fluoro-3-phenoxybenzyl 3-(n-pentyloxy)-2,2-dimethylcyclopropanecarboxylate,
α-cyano-4-fluoro-3-phenoxybenzyl 3-(n-propoxy)-2,2-dimethylcyclopropanecarboxylate,
α-cyano-4-fluoro-3-phenoxybenzyl 3-(n-butoxy)-2,2-dimethylcyclopropanecarboxylate, and
α-cyano-4-fluoro-3-phenoxybenzyl 3-(n-hexyloxy)-2,2-dimethylcyclopropanecarboxylate.

EXAMPLE 14

To a stirred solution of α-cyano-4-fluoro-3-phenoxybenzyl alcohol (437 mg., 1.8 mmol), 3-(n-pentyloxy)-2,2-dimethylcyclopropanecarboxylic acid (2.0 mmol) and 4-dimethylaminopyridine (0.65 mmol) in 20 ml of methylene chloride and 2 ml of DMF is added N,N'-dicyclohexylcarbodiimide (2 mmol). The reaction mixture is stirred, under nitrogen, for about two hours and then filtered and extracted with water. The aqueous phase is extracted with ether. The combined organic phases are washed with saturated aqueons sodium bocarbonate, water and saturated aqueous sodium chloride, dried over calcium sulfate and solvent evaporated.

The crude product is chromatographed on a rotary chromatograph eluting with ether/hexane to yield α-cyano-4-fluoro-3-phenoxybenzyl 3-(n-pentyloxy)-2,2-dimethylcyclopropanecarboxylate.

In the same way, there is prepared α-cyano-2-fluoro-5-phenoxybenzyl 3-(n-pentyloxy)-2,2-dimethylcyclopropanecarboxylate from α-cyano-2-fluoro-5-phenoxybenzyl alcohol.

EXAMPLE 15

(A) Using the procedure of Example 14, α-cyano-4-fluor-3-phenoxybenzyl alcohol is reacted with each of the acids, 3-(i-butoxy)-2,2-dimethylcyclopropanecarboxylic acid, 3-(s-butoxy)-2,2-dimethylcyclopropanecarboxylic acid and 3-(i-pentyloxy)-2,2-dimethylcyclopropanecarboxylic acid to yield α-cyano-4-fluoro-3-phenoxybenzyl 3-(i-butoxy)-2,2-dimethylcyclopropanecarboxylate α-cyano-4-fluoro-3-phenoxybenzyl 3-(s-butoxy)-2,2-dimethylcyclopropanecarboxylate α-cyano-4-fluoro-3-phenoxybenzyl 3-(i-pentyloxy)-2,2-dimethylcyclopropanecarboxylate (B) Using the procedure of Example 14, each of 4-fluoro-3-phenoxybenzyl alcohol and 2-fluoro-5-phenoxybenzyl alcohol is reacted with 3-(i-butoxy)-2,2-dimethylcyclopropanecarboxylic acid to yield 4-fluoro-3-phenoxybenzyl 3-(i-butoxy)-2,2-dimethylcyclopropanecarboxylate and 2-fluoro-5-phenoxybenzyl 3-(i-butoxy)-2,2-dimethylcyclopropanecarboxylate.

What is claimed is:

1. A compound of the formula (A):

$$R^1-W-CH\underset{X\diagup C\diagdown X'}{---}CH-\underset{\overset{\parallel}{O}}{C}-O-\underset{F}{CH}-\text{Ar}-R-\text{Ar}-R'_p \quad (A)$$

wherein:
W is oxygen or sulfur;
X is lower alkyl or halogen;
X' is hydrogen, lower alkyl or halogen;
$R^1$ is lower alkyl, lower haloalkyl, lower alkenyl, lower haloalkenyl, or the group $$\underset{Z}{\overset{Y_t}{\diagdown}}\text{Ar}-$$

in which,
t is zero, one, two, three or four;
Y is independently selected from hydrogen, lower alkyl, lower haloalkyl, lower alkoxy, lower alkylthio, lower alkylcarboxyl, lower alkoxycarbonyl, lower aryloxy, halogen, cyano, nitro and lower haloalkylthio;
Z is independently selected from the values of Y, cycloalkyl, and lower haloalkoxy; or together with Y forms a methylenedixoy group;
R is oxygen, sulfur, methylene or carbonyl;
R' is hydrogen, fluoro, bromo, chloro, trifluoromethyl, methyl, methoxy or methylthio;
p is zero, one or two; and
$R^2$ is hydrogen, cyano, methyl or ethynyl.

2. A compound according to claim 1 of the formula:

$$R^1-W-CH\underset{X\diagup C\diagdown X'}{---}CH-\underset{\overset{\parallel}{O}}{C}-O-\underset{F}{CH}-\text{Ar}-O-\text{Ar}-R'_p$$

3. A compound according to claim 2, wherein each of X and X' is methyl.

4. A compound according to claim 1 of the formula:

$$R^1-W-CH\underset{X\diagup C\diagdown X'}{---}CH-\underset{\overset{\parallel}{O}}{C}-O-\underset{F}{CH}-\text{Ar}-O-\text{Ar}-R'_p$$

5. A compound according to claim 4 wherein each of x and X' is methyl.

6. A compound according to claim 1 of the formula:

$$R^1-W-CH\underset{X\diagup C\diagdown X'}{---}CH-\underset{\overset{\parallel}{O}}{C}-O-\underset{}{CH}-\underset{F}{\text{Ar}}-O-\text{Ar}-R'_p$$

7. A compound according to claim 6 wherein each of X and X' is methyl.

8. A compound according to claim 3 wherein p is zero and W is oxygen.

9. A compound according to claim 8 wherein $R^1$ is lower alkyl or the group $$\underset{Z}{\overset{Y_t}{\diagdown}}\text{Ar}-$$

wherein t is zero or one, Y is hydrogen, methyl, chloro, or fluoro, and Z is hydrogen, methyl, chloro, fluoro, bromo or trifluoromethyl.

10. A compound according to claim 9 of the formula:

$$\underset{Z}{\overset{Y_t}{\diagdown}}\text{Ar}-O-CH\underset{CH_3\diagup C\diagdown CH_3}{---}CH-\underset{\overset{\parallel}{O}}{C}-O-\underset{F}{CH}-\text{Ar}-O-\text{Ar}$$

wherein $R^2$ is hydrogen or cyano.

11. A compound according to claim 10, wherein t is zero and Z is in the para position.

12. A compound according to claim 11 wherein Z is chloro.

13. The compound, 4-fluoro-3-phenoxybenzyl 3-(n-pentyloxy)-2,2-dimethylcyclopropanecarboxylate, according to claim 9.

14. The compound, α-cyano-4-fluoro-3-phenoxybenzyl 3-(n-pentyloxy)-2,2-dimethylcyclopropanecarboxylate, according to claim 9.

* * * * *